United States Patent [19]

Wick

[11] Patent Number: 5,064,422
[45] Date of Patent: Nov. 12, 1991

[54] TWIN PATCH APPLICATOR

[75] Inventor: John J. Wick, Williston, Vt.

[73] Assignee: Bertek, Inc., Swanton, Vt.

[21] Appl. No.: 599,686

[22] Filed: Oct. 18, 1990

[51] Int. Cl.⁵ .............................................. A61F 13/00
[52] U.S. Cl. ..................................... 604/307; 424/449
[58] Field of Search ............................. 604/304–307, 604/289; 128/156; 424/447–449

[56] References Cited

U.S. PATENT DOCUMENTS

| | | | |
|---|---|---|---|
| 716,265 | 12/1902 | McAllister | 604/307 |
| 2,807,262 | 9/1957 | Lew | 604/307 |
| 3,342,183 | 9/1967 | Edenbaum | 604/307 |
| 3,900,027 | 8/1975 | Keedwell | 604/307 |
| 4,666,441 | 5/1987 | Andriola et al. | 604/304 |
| 4,911,707 | 3/1990 | Heiber et al. | 604/307 |
| 4,917,676 | 4/1990 | Heiber et al. | 604/307 |
| 4,917,688 | 4/1990 | Nelson et al. | 128/156 |

Primary Examiner—C. Fred Rosenbaum
Assistant Examiner—Sharon Finkel
Attorney, Agent, or Firm—Lerner, David, Littenberg, Krumholz & Mentlik

[57] ABSTRACT

Devices for applying a plurality of active agents to the skin of a patient are disclosed including a liner layer with a releasable surface, a carrier layer, and a plurality of active agent carriers on the surface of the carrier layer, with the releasable surface of the liner layer in contact with the surface of the carrier layer including the active agent carrier and the two surfaces being releasably heat sealed together at least at a location between the plurality of active agent carriers in order to physically separate them prior to removal of the liner layer from the carrier layer.

18 Claims, 2 Drawing Sheets

TWIN PATCH APPLICATOR

FIELD OF THE INVENTION

The present invention relates to devices for applying active agents to a patient. More particularly the present invention relates to devices for applying more than one active agent to the skin or mucosa of a patient. Still more particularly, the present invention relates to devices for applying active agents and film layers to the skin or mucosa of a patient. Still more particularly, the present invention relates to the application of devices allowing for the topical and systemic administration to the host or administration through the skin or mucosa of the host over a period of time.

BACKGROUND OF THE INVENTION

In connection with the efforts which have been expended in order to develop devices for applying active agents, as well as active agents and film layers, to the skin of a host or patient, a recent significant development in this regard is set forth in U.S. Pat. No. 4,915,102. In that patent a device for either transferring a film layer to the skin or mucosa of a patient or host, or for the application of a film layer combined with an active agent carrier, is disclosed. The devices which are shown in this patent permit the application of a film layer, or a film layer in combination with an active agent carrier, to the skin in a most simple and facile manner, particularly as compared to the prior art up to that time.

As is spelled out in the background section of U.S. Pat. No. 4,915,102, aside from efforts to apply film layers per se, there have also been considerable efforts in connection with the application of active agent carriers themselves. This patent thus includes a discussion of the various transdermal administration systems, including Ciba-Geigy's TRANSDER®-NITRO and TRANSDERM®-V systems, as well as a significant improvement represented by U.S. Pat. No. 4,573,996, which is seepage-resistant during use, therefore eliminating prior problems with contamination which were previously encountered in such devices.

There have also been a number of systems which have attempted to employ multiple compartments for the administration of drugs and the like. An early such device is shown in U.S. Pat. No. 4,460,370, FIGS. 6 and 7 of which depict transdermal delivery patches having two compartments separated by a dam to prevent mixing of the contents of these compartments. The reservoirs in the devices of the '370 patent are filled with the drug to be delivered through an aperture in the top of the patch separately and are maintained separate from each other by means of the dam therebetween.

Two later patents directed to transdermal drug delivery systems with multiple reservoirs are disClosed in U.S. Pat. Nos. 4,917,676 and 4,911,707. These patents also employ membranes to separate various compartments, and, in fact, use combinations of permeable and impermeable membranes to enclose these separate compartments and separate them from each other. These patents also disclose use of a heat seal as the barrier between the reservoirs which are of sufficient pressure to prevent bursting. The compartments in these patents are said to hold both an activating agent and an agent which is to be activated thereby.

Another such multi-compartmentalized device is shown in U.S. Pat. No. 4,666,441. In this case the barriers between the compartments are formed by membranes, but at column 5, lines 12-15 thereof it is also stated that when they are not burstable they are heat sealed. Within the compartments themselves, the 441 patent discloses a potential use of different concentrations of the same drug or different vehicles having different drug release rates. The patent also discloses the potential use of different drugs in different compartments. However, the structure of the device shown in the '441 patent employs a single membrane to define more than one reservoir; that is, by heat sealing the area encompassed by the membrane to subdivide the membrane into separate reservoirs. The object is to obtain intermixing between the reservoirs during application, and not to keep the two systems separate even after application to the patient simultaneously. Thus, even where the '441 patent discusses simultaneous application of different drugs, that is only in the context of the use of non-burstable boundaries between the compartments to maintain them separate during application.

SUMMARY OF THE INVENTION

In accordance with the present invention, the deficiencies in the prior art have now been overcome by applicant's invention of a device for applying a plurality of active agents to a patient comprising a liner layer including a first surface and a second surface, the first surface of the liner layer comprising a releasable surface, a carrier layer including a first surface and a second surface, and a plurality of active agent carrying members disposed on the first surface of the carrier layer, the first surface of the liner layer being releasably heat sealed to the first surface of the carrier layer at least at a location between the plurality of active agent carrying members so as to physically separate the plurality of active agents prior to separation of the liner layer from the carrier layer.

In a preferred embodiment the device includes a plurality of film layers disposed on the first surface of the carrier layer between the carrier layer and the active agent carrying members whereby the active agent carrying members are applied to the patient along with the film layers.

In one embodiment of the device of the present invention, the active agent carrying members comprise adhesive layers carrying the active agents. Preferably, adhesive layers are used having a thickness of between about 0.5 and 5 mils.

In accordance with another embodiment of the device of the present invention, the first surface of the liner layer is releasably heat sealed to the first surface of the carrier layer at least around the entire periphery of each of the plurality of active agent carrier members.

In accordance with another embodiment of the device of the present invention, the plurality of active agent carrier members comprises a plurality of reservoirs containing the active agents, release means for the controlled release of the active agents from the plurality of reservoirs, and a plurality of active agent impermeable barrier layers between the plurality of reservoirs in the carrier layer whereby the plurality of active agents may only be released from the inner surface of the plurality of reservoirs towards the patient upon application of the plurality of active agent carriers to the patient.

In accordance with a preferred embodiment of the device of the present invention in which the device includes a plurality of film layers, the device also includes a first adhesive layer interposed between the first surface of the carrier layer and the plurality of film layers for maintaining the plurality of film layers in contact with the carrier layer when the liner layer is separated from the carrier layer, and a second adhesive layer interposed between the plurality of film layers and the first surface of the liner layer, the first adhesive layer having a first coefficient of adhesion and the second adhesive layer having a second coefficient of adhesion, the first coefficient of adhesion of the carrier layer to the plurality of film layers being less than the second coefficient of adhesion of the plurality of film layers to the patient, whereby upon application of the plurality of film layers to the patient with the second adhesive layer therebetween the plurality of film layers adheres to simultaneously be removed from the carrier layer. Preferably, the second adhesive layer comprises an adhesive layer covering at least the entire surface of the plurality of film layers.

BRIEF DESCRIPTION OF THE DRAWINGS

Referring to the following detailed description, that description can be more readily understood with reference to the Figures which follow, in which.

DETAILED DESCRIPTION

Figure 1:
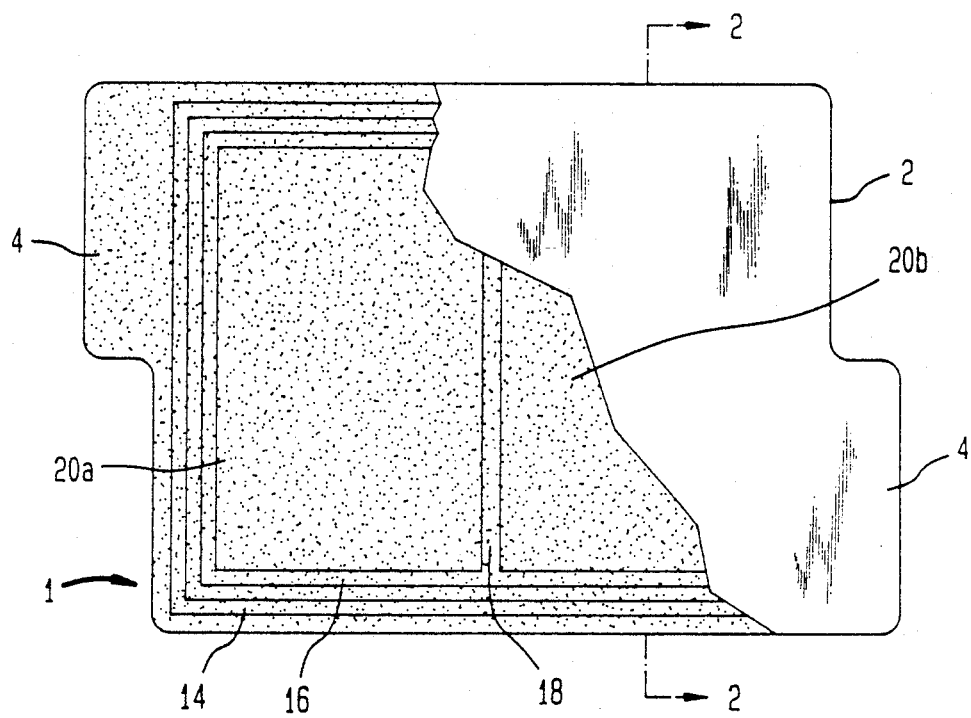
FIG. 1 is a top, elevational, partially torn away view of a device of the present invention, showing the liner layer thereof.
Figure 2:
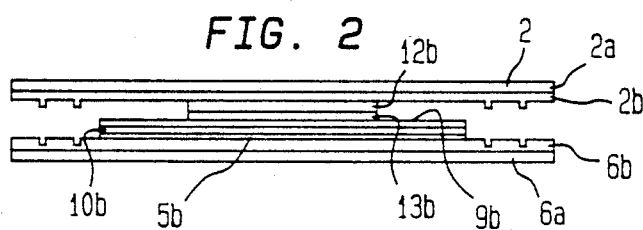
FIG. 2 is a side, cross-sectional view of the device of the present invention as shown in FIG. 1.

Referring to the Figures, in which like numerals refer to like portions thereof, FIG. 1 shows a device of the present invention. More particularly, FIG. 1 shows the portion of the device in which the liner layer is exposed, while FIG. 3 shows the portion of the device including the carrier layer as well as the active agent carrying members, and FIG. 2 shows a cross section of the entire device in its sealed configuration.

Referring first to FIG. 1, the liner layer 2 is basically intended to protect the active agents as well as any film layers used in the device of this invention prior to use, and to render them transportable while not interfering with their ultimate application. Furthermore, in accordance with this invention, the liner layer 2 must be heat sealed to the carrier layer 6 in order to not only protect the active agents, but to maintain them separate from each other for the purposes discussed herein. The liner layer 2 can therefore comprise various layers, including paper or paper-containing layers or laminates; various thermoplastics, such as extruded polyolefins, such as polyethylene; various polyester films; foil liners; other such layers, including fabric layers, coated or laminated to various polymers, as well as extruded polyethylene, polyethylene terephthalate, various polyamides, and the like. However, this liner layer 2 must have an inner surface which is releasable with respect to the materials or layers with which it is initially in contact, such as the adhesive layers 9a and 9b on the carrier layer 6 (see FIG. 2). It should therefore include a release coating, such as where a paper layer or the like is employed. This can be done in a conventional manner, such as by including a silicone or Teflon coating on the surface thereof. However, a particularly preferred embodiment of the present invention includes a laminate of an outer foil layer 2a and an inner layer 2b of plastic, such as polyethylene or the like, which is rendered releasable not only by means of a siliconized coating, but which includes an embossed or roughened surface. Embossment of this surface can be accomplished by a number of conventional methods. In general, preparation of embossed surfacing can be accomplished by the use of male-female tooling, preferably enhanced by the application of heat. The principal intention of this embossment process is to roughen the surface or render it uneven so that less than the entire surface will be in physical contact with the corresponding inner surface of the carrier layer 6 discussed in more detail below. This embossment technique is thus carried out on the liner layer 2 prior to completion of the manufacture of this device by combining the liner layer 2 with the carrier layer 6. The actual pattern of embossment carried out can vary, and in some instances may involve embossment of large contiguous areas of the liner layer 2. For example, where an active agent carrier or the like is included on the carrier layer 6, it is possible to emboss the entire area, or at least those portions of the area of the liner layer 2 corresponding to the area surrounding the active agents or active agent carriers. Again, however, the overall intent behind doing so is to reduce the area of direct contact between the carrier layer and the liner layer so as to facilitate subsequent separation thereof. Preferably, approximately 30% of the surface of the liner layer will thus be embossed. The particular design of the embossment, such as the production of a grainy texture or the like, is a matter of choice within the parameters discussed above. The presence of the embossed surface on the inner surface of the liner layer 2 is thus extremely significant in preventing the liner layer 2 from sticking or adhering to the carrier layer 6, which would cause these layers to fail to properly separate when it is desired to use the device of the present invention. This ease of operation is an important element in commercialization of these devices. The selection of a particular liner layer 2 will also depend upon other ultimate requirements of the particular device in question, including whether there is a desire for a transparent or opaque liner, etc. It can thus be seen that essentially throughout the area of contact between the carrier layer 6 and the liner layer 2, although there is adhesive present on at least a portion of the side of the carrier layer 6 which is in contact with the liner layer 2 in order to maintain these two layers in contact, that the seal throughout that area is "peelable," or releasable, by merely pulling apart the edge of the liner layer 2. At the same time, when this is done the active agent carriers, possibly in combination with film layers, remain in contact with the lower surface of the carrier layer 6 because of the relationship between the adhesive materials in the adhesive layer maintaining the active agent carrier in contact with the carrier layer 6 vis-a-vis the adhesive layer between the surface of the active agent carrier, or film layers, and/or carrier layer 6 and the liner layer 2.

Figure 3:
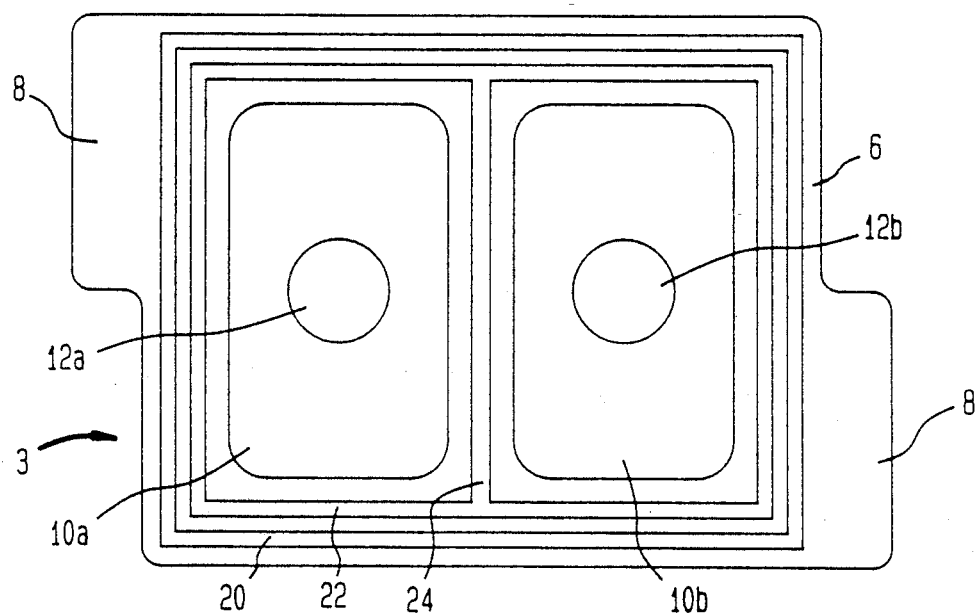
FIG. 3 is a top, elevational view of a carrier layer used in connection with the device of the present invention.

Turning to FIG. 3, this portion of the device of the present invention includes carrier layer 6, upon which are maintained the active agents, either alone or in combination with film layers. Thus, in the embodiment shown in FIG. 3 the active agent carriers 12a and 12b are placed upon separate film layers 10a and 10b, both of which are to be applied to the skin simultaneously. Use of the film layers is not essential to this invention, however, and an embodiment of this invention includes only the active agent carriers 12a and 12b, which can be in a number of forms, including that of the active agent carriers 128a and 128b which are discussed below with reference to FIGS. 4 through 6 hereof. In that case, however, means must be provided to ensure that these active agent carriers 128a and 128b will remain associated with the carrier layers upon separation of the liner layer therefrom. Thus, in these cases, as is discussed in more detail below, a separate adhesive layer is applied between the active agent carriers and the carrier layer therefor.

The carrier layer 6 itself should be flexible enough to generally follow the contour of the area of the host where the device is to be applied. On the other hand, it should have enough strength and substance so as to serve its function of carrying the active agent carriers and possibly the film layers without wrinkling, etc. The actual material from which the carrier layer 6 can be produced can therefore include a variety of different materials. Some suitable materials for this layer include, for example, polyethylene, polypropylene, polyvinylidene chloride, polyethylene terephthalate, polyesters, polyamides, and others, as well as laminates of two or more of these layers with each other or with additional layers, such as foil, paper, various fabrics, etc., but in these cases preferably with the polymer layer on the inside, i.e., in contact with and thereby carrying the active agent carrier, and possibly film layers 10a and 10b. Therefore, in the preferred embodiment of the invention as is shown in FIG. 2 the carrier layer 6 comprises a laminate of an outer foil layer 6a and an inner layer 6b of plastic, such as polyethylene or the like.

With respect to the active agent carriers 12a and 12b themselves, in this embodiment as shown in FIGS. 1-3, they basically comprise a monolithic active agent carrier. Thus, in essence these monolithic active agent carriers basically comprise an adhesive layer which is admixed with the active agent or drug component. Thus, in the embodiment shown in FIG. 2, this monolithic active agent carrier 12b is supported on an occlusive barrier layer 13b. This layer is occlusive primarily with respect to solvents or enhancers which are contained along with the active agent in the monolithic active agent carrier 12b. Thus, the presence of occlusive barrier layer 13b prevents the escape or seepage of enhancer towards the carrier layer 6 so that the effectiveness of the active agent carrier 12b is not lost or diminished. The occlusive barrier layer 13b can itself comprise the types of plastic components as It is also noted that, in accordance with the embodiment shown in FIGS. 1-3, film layer 10b supports the active agent carrier 12b. Furthermore, the surface of film layer 12b includes adhesive layer 9b thereon. Subsequent to application of the film layer and the active agent carrier layer to the skin the principal function of holding these components to the skin will be met by the presence of this adhesive layer 9b. On the other hand, in an embodiment of the present invention where film layer 10b is not provided, and an active agent carrier such as active agent carrier 12b alone is to be applied to the skin, the requirements for the adhesive characteristics of the adhesive in the active agent carrier 12b are increased. In the embodiments of FIGS. 1-3, this can pose a problem. For this reason, the embodiment shown, which includes film layer 10b, is highly preferred. In particular, when the monolithic active agent carrier 12b is prepared and drug and enhancer or solvent is mixed with adhesive, the adhesive characteristics of the adhesive component will be reduced. Thus, difficulty can be created in terms of rendering the adhesive strong enough to meet the requirements for applying same to the skin in a relatively permanent fashion. Again, however, when the adhesive 9b is present in connection with film layer 10b, any reduction in the adhesive characteristics of the monolithic active agent carrier 12b will not be detrimental. It is, in fact, for this reason that yet another embodiment of the present invention exists, i.e. one in which the active agent carrier represented by reference numeral 12b includes no adhesive component at all; for example, where it is a gel or hydrogel component.

In particular, hydrogels of use herein can be formed using the following water soluble or water insoluble gums or resins, with or without known crosslinking agent: agarose, alginates, alkyl and hydroxyalkylcellulose, amylopectin, arabinoglactin, carboxymethylcellulose, carrageenan, eucheuma, fucoidan, furcellaran, gelatin, guar gum, gum agar, gum arabic, gum ghatti, gum karaya, gum tragacanth, hydroxethyl cellulose, hydroxypropyl cellulose, hypnea, keratin, laminaran, locust bean gum, pectin, polyacrylamide, poly(acrylic) acid and homologs, polyethylene glycol, poly(ethylene) oxide, poly(hydroxyalkyl methacrylate), polyvinyl alcohol, polyvinylpyrrolidone, propylene glycol alginate, starch and modified analogs, tamarind gum, n-vinyl lactam polysaccharides, and xantham gum. In addition, such hydrogels can also be formed by the copolymerization and crosslinking of both hydrophilic and hydrophobic monomers, such as hydroxyalkyl esters of acrylic and methacrylic acids, derivatives of acrylamide and methacrylamide, and n-vinyl-2-pyrrolidone, alkyl acrylates and methacrylates, vinyl acetate, acrylonitrile and styrene.

Again, when used in connection with film 10b the adhesive layer 9b thereon will hold the entire device, including the active agent carrier 12b, on the skin whether or not it is adhesive in nature.

Figure 4:
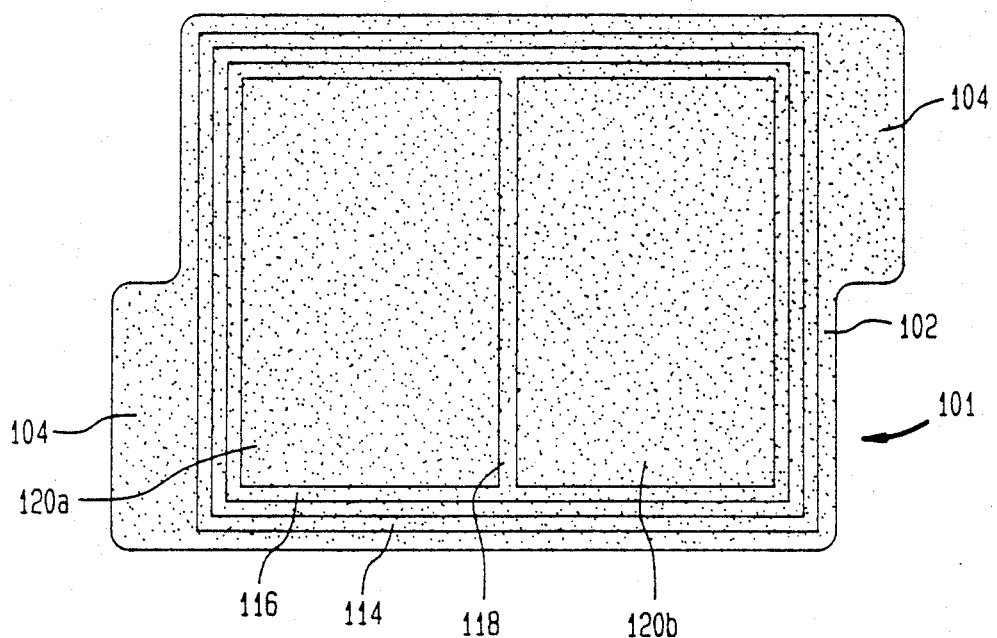
FIG. 4 is a top, elevational view of a liner layer for use in another embodiment of the device of the present invention.
Figure 5:
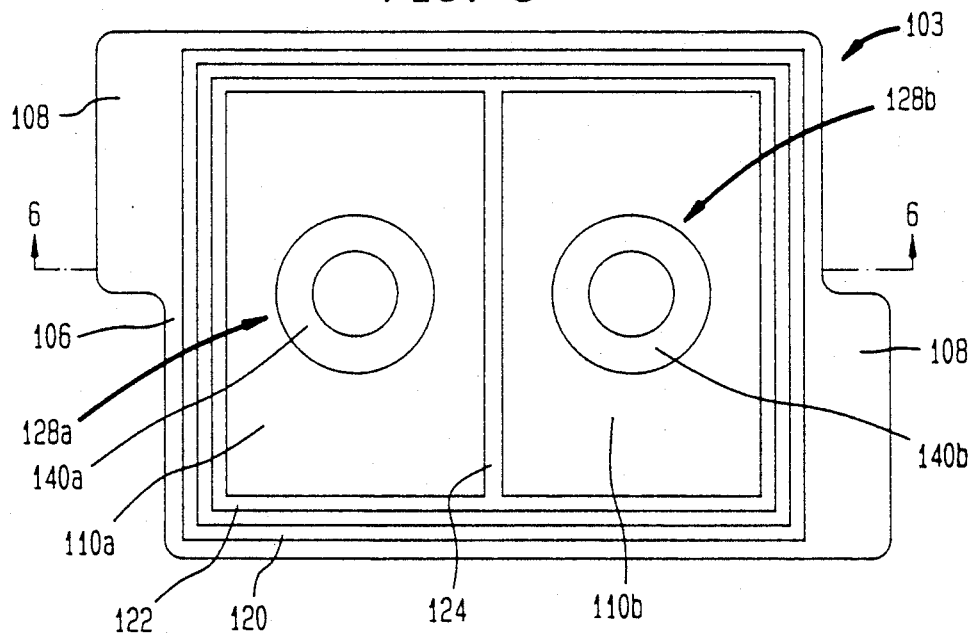
FIG. 5 is a top, elevational view of another carrier layer for use in connection with another embodiment of the device of the present invention.
Figure 6:
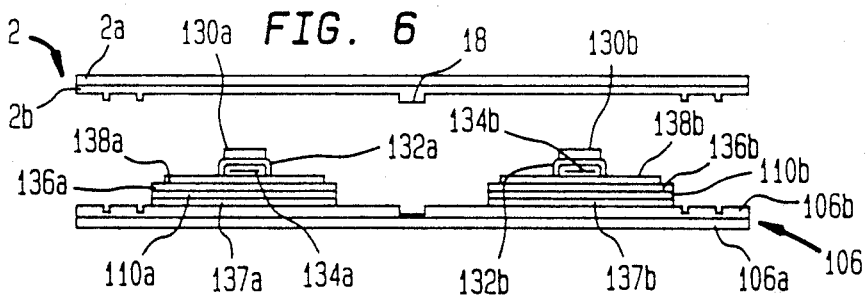
FIG. 6 is a side, cross-sectional view of the combination of the carrier layer shown in FIG. 5 with the liner layer shown in FIG. 4 taken along lines 6—6 thereof.

In another embodiment of the device of the present invention, as is shown in FIGS. 4-6, the active agent carriers 128a and 128b are applied to the surface of the carrier layer 106 by means of adhesive layers 136a and 136b (in the embodiment shown, film layers 110a and 110b are employed, and are thus interposed between the active agent carriers 128a and 128b and carrier layer 106 by means of further adhesive layers 137a and 137b). The active agent carriers 128a and 128b themselves include the active agent contained in separate and distinct reservoirs 134a and 134b created by backing members 138a and 138b and membranes 132a and 132b, which are sealed to each other about the circumference or perimeter of the membrane, preferably by means of a heat seal. Active agent permeable adhesive layers 130a and 130b can be applied to the surface of the membranes opposite the reservoirs.

Referring now to the embodiments both in FIGS. 1-3 and 4-6, in either case, the active agent carriers are maintained in contact with the surface of film layers 10a and 10b (and 110a and 110b). In the case of the embodiment in FIGS. 4-6, this is accomplished by means of adhesive layers 136a and 136b. The essential requirement here is that the active agent carriers, either alone or in combination with the film layers, must be adhered to the carrier layers 6 with sufficient strength to maintain same when these active agent carriers and/or film layers are exposed or uncovered by removing the liner layer therefrom, while at the same time this bond must be sufficiently weak in relative terms so that it will readily peel off or be removable from the carrier layers 6 after the active agent carriers, including the film layers, have been to the skin, by means of the adhesive layers 9a and 9b (and 136a and 136b) discussed herein. In this connection, this is accomplished by the relationship between the strength of adhesive layers 5a and 5b on the one hand, and 9a and 9b (also possibly in combination with the adhesive in layers 12a and 12b) on the other hand, in connection with the embodiment shown in FIG. 2 hereof. In this regard, the adhesive layer between the carrier layer and the film layers has a coefficient of adhesion which is less than the coefficient of adhesion of the adhesive layer between the film layers and the liner layer. In this manner, upon application of the film layers and the active agent carriers to the patient with the aforementioned adhesive layers 9a and 9b therebetween, the plurality of film layers will adhere to the patient and be simultaneously removed from the carrier layer vis-a-vis adhesive layers 5a and 5b. The same principle applies with respect to the embodiment shown in FIGS. 4-6 hereof.

In order to produce the overall device shown in cross-section in FIG. 2, the liner player 2 is brought into face-to-face contact with the carrier layer 6 with the active agents (and possibly film layers) therebetween. In accordance with the critical element of the present invention, and even though these layers are in intimate contact by means of the adhesive layers 9a and 9b (and 136a and 136b) which cover a substantial portion of the area represented by the carrier layer 6 by covering the face of the film layers 10a and 10b (and 110a and 110b), heat seals are also provided between the liner layer 2 and the carrier layer 6 in a particular critical configuration. Referring again to FIGS. 1 and 3, at a location between the active agent carriers 12a and 12b (or 112a and 112b) such a releasable heat seal is provided. The location of that heat seal with respect to the carrier layer 6 is shown by reference numeral 18 in FIG. 1, and with reference to the liner layer 2 is shown by reference numeral 24 in FIG. 3. This is provided as a "peelable seal38 between the carrier layer 6 and the liner layer 2. While the precise compositions of the carrier and liner layers are discussed in more detail in this application, the nature of the facing layers therebetween will be significant in creating such a "peelable seal." In this regard, it should be noted, for example, where the two facing layers comprise inner polyethylene layers, the creation of such a "peelable seal" is then accomplished in the manner described in U.S. Pat. No. 4,710,191, the disclosure of which is incorporated here by reference thereto. In particular, in that patent it is disclosed that such a "peelable seal" can be created by the incorporation of a release coating on the inner surface of a layer such as liner layer 2 so as to render the heat sealed area then created between these two layers, in this case between liner layer 2 and carrier layer 6, by weakening the thermal bond created therein. It is also disclosed in this patent that one alternative for achieving this result is to employ two different materials as the inner layers for the liner layer 2 and the carrier layer 6, such as polyethylene and polypropylene, etc. In such a case no release coating would then be required on the inner surface of the liner layer 2, at lease for the purposes of creating such a "peelable seal" at these locations. In general, the purpose of this "peelable seal" is not only to provide the advantages discussed above in terms of separating the active agent carrier and preventing migration of the enhancers, solvents, or the like, which would then adversely effect the transfer rates of the various drugs contained therein, but at the same time these "peelable seals" permit the ready separation of the liner layer 2 and the carrier layer 6. For example, if two polyethylene layers were heat sealed together in the manner discussed above without a release coating, such as a silicon layer therebetween, the two layers would essentially melt together, and such separation would not be readily achieved. Thus the nature of these "peelable seals" is an important feature of the present invention.

Referring again to FIGS. 1 and 3, "peelable seals" which critically separate the two active agent carriers 12a and 12b thereof are located not only therebetween, but extend along path 16 so as to surround both active agent carrier 12a and active agent carrier 12b, as well as their respective film layers. Furthermore, a separate continuous heat seal 14 separated from heat seal 16 surrounds the entire device including both active agent carriers 12a and 12b.

In this manner, each of the active agent carriers, as well as their respective film layers, is isolated prior to separation of the liner layer 2 from the carrier layer 6. The significance of this separation has been discussed above, and primarily relates to the fact that where, for example, different drugs are to be applied in connection with active agent carriers 12a and 12b, it will generally be necessary to carefully specify each of the formulations for each of these active agents. These formulations will include the use of relatively volatile solvents or enhancers, such as ethanol and the like, which are utilized in connection with these active agents. The term "enhancer" is meant to refer to those additives which have the effect of opening the patient's pores and thus facilitating delivery of the drugs or other active agents thereby. In general, however, the primary purpose of these solvents and/or other carriers is to determine the rate of transdermal application which will apply when these active agents are applied to the skin of the patient. Since this delivery rate is a critical element in the use of any such active agents, any premature migration or mixing of these solvents or carriers will alter this delivery rate, with obvious untoward consequences. Placement of the heat seals described above between these active agent carriers, however, will prevent such migration or mixing, and thus permit maintenance of the critical and carefully devised delivery rates and potency for each of the separate active agents therein, and at the same time will have no adverse effect upon use of this device, i.e., the carrier and liner layers are still readily separated when it is desired to apply these active agents to the patient's skin. It is further noted that the placement of such a heat seal between the active agents hereof provides an area therebetween which could be used for separation of the device into separate devices. This can be facilitated by merely widening the area of this peelable heat seal between the active agent carriers, for example, to provide a ¼ inch heat-sealed strip therebetween. Thus, by using a scissors to cut through such enlarged areas 18 and 24 prior to separation of the carrier layer from the liner layer, two separate devices can be readily provided from the single device manufactured therein. This provides yet another utility for the devices of the present invention.

The adhesive layers 9a and 9b for maintaining the active agent carriers 12a and 12b and the film layers 10a and 10b on the surface of the skin of the host (as well as the adhesive layers 136a and 136b in the embodiment of FIGS. 4-6) should preferably be hypoallergenic, since they are being applied to the skin. More particularly, and referring specifically to the embodiment shown in FIGS. 4-6, the portion of such adhesive layers which are at the location of the membranes 132a and 132b of the active agent carriers 112a and 112b, must be active agent permeable adhesive layers, i.e., so the active agent can permeate through these layers when they are eventually interposed between the active aqent and the skin of the host into which they are intended to penetrate. These portions of these adhesive layers are designated by reference numerals 130a and 130b in FIG. 6. However, these active agent permeable adhesive layers 130a and 130b should be limited to the area of the membranes themselves, and the remaining portion of the adhesive necessary for coating the surface of the liner layers 6 and 106 can comprise active agent impermeable adhesive layers which are discussed in more detail below. The reason for this is that the use of an active agent permeable adhesive over the entire surface of the liner layer or at least beyond the periphery of the active agent carriers themselves would concomitantly increase the drug delivery surface, and the treatment dosage for the particular drug delivery system in question would be undesirably altered thereby. In addition, in the embodiment where film layers are also being transferred along with the active agent carriers, the remainder of the surface of the film layers 10a and 10b (and 110a and 110b) can comprise layers of active agent impermeable adhesive, and more particularly a relatively strong adhesive for maintaining the film layers in firm contact with the skin of the host. In that case, the presence of an adhesive layer on the surface of the active agent carrier becomes of little significance, since that surface will be maintained in contact with the skin by means of the surrounding adhesive layers 11a and 11b, and 111a and 111b. However, it is still preferable in that case to nevertheless employ an adhesive layer for the area of the active agent carrier, at least for assuring the maintenance of contact between the active agent carrier and the skin of the host. For that purpose, a contact type adhesive, of substantially less strength, can thus be utilized.

The film layers 10a and 10b, or 110a and 110b, and the impermeable adhesive layers 9a and 9b, or 136a and 136b, thus form a pocket surrounding the backing members 13a and 13b, and 138a and 138b, the active agent carriers 12a and 12b, as well as reservoirs 134a and 134b, membranes 132a and 132b, and active agent permeable adhesive layers 130a and 130b, so that when the device is adhered to the skin or mucosa, the active agent can be released from the active agent carriers 12a and 12b, as well as through the membranes 132a and 132b and through the active agent permeable adhesive layers 130a and 130b to provide a continuous dose of the active agent therethrough, but cannot permeate through the film layers or radially outwardly through the active agent impermeable adhesive layers.

The outer surface member, that is the member of the active agent carrier which is in contact with the film layers 110a and 110b in the embodiment of FIGS. 4-6, be they separate overlay covering layers or backing members 138a and 138b described above, is preferably a thin film or sheet. In many instances, because of the area of skin to which the device is to be attached, the device is flesh colored for cosmetic reasons. Preferably, it is a clear polyester layer, which is occlusive with respect to the active agent or drug, but it can be dyed various colors, or include printed matter thereon. The outer surface layer normally provides support and a protective covering for the device. In a most preferred embodiment these layers comprise highly occlusive layers of polyethylene terephthalate or of polyvinylidene chloride compounds such as SARAN.

The outer surface layer is preferably made of a material or combination of materials which is substantially impermeable to the layer or layers with which it can be in contact, i.e., to the active agent, the impermeable and permeable adhesives, etc. However, a primary purpose is to prevent seepage of the active agent through the outer surface layer of the device so that, if the outer surface layer is coated on the surface in contact with the remainder of the device with the active agent impermeable adhesive layer, this impermeable adhesive layer will perform this purpose even if the outer surface layer is not totally impermeable to the active agent. Thus, it is not necessary in all instances that the outer surface layer be impermeable to the active agent, although in most instances, it normally is. By substantially impermeable, we mean that the other components in contact with the layer or component under consideration will not appreciably permeate through such layer or component for the normal period of use and storage of the device, see the discussion of impermeability, infra.

The actual material used for the outer surface layer, i.e., the overlay covering and/or the backing members 138a and 138b, will depend on the properties of the materials in contact therewith. Some suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride (e.g., SARAN), paper, cloth, and aluminum foil. The material which forms this outer surface layer may be flexible or non-flexible. Preferably, a flexible outer surface layer is employed to conform to the shape of the body member to which the device is attached.

Preferably, the material which forms the overall covering layer and/or the backing members 138a and 138b are a film or a composite film. The composite can be a metallized (e.g., aluminized) film or a laminate of two or more films or a combination thereof. For example, a laminate of polyethylene terephthalate and polyethylene or a polyethylene/metallized polyethylene terephthalate/polyethylene laminate can be employed. The preferred polymers include polyethylene, polypropylene, polyvinyl chloride, polyethylene terephthalate, and polyvinylidene chloride (SARAN). Most particularly, a highly preferred composition of the present invention employs polyvinylidene chloride or SARAN as the backing members 138a and 138b in conjunction with a film layer 110a and 110b which comprises the PEBAX materials discussed below. Thus, while the SARAN component is highly occlusive with respect to the materials in question, it also is relatively stiff or hard, and therefore use of a very soft and flexible film, such as those discussed below as the film layers 110a and 110b hereof, provides an excellent combination from the point of view of comfort and application to the user.

The above discussion also applies to the embodiments in which only active agent carriers are being applied to the skin, and no film layers are included therein. In these embodiments, the adhesive layers between the carrier layers and the outer surface of the active agent carriers, such as backing members 138a and 138b, will comprise a pressure sensitive adhesive, such as a cross-linkable acrylic copolymer.

These are the same adhesive layers 137a and 137b which are used to adhere the film layers 110a and 110b to the carrier layer 106 when the film layers 110a and 110b are used in conjunction with the active agent carriers 112a and 112b. In either case, the adhesive itself can be an acrylic copolymer adhesive such as Avery Chemical Company's AS-351 HSX, preferably at a coating weight of between about 25 and 35 g/m$^2$. This pressure sensitive adhesive is a cross-linkable polymer which dries to provide a permanently tacky film having a total solids content of about 52%, a Brookfield viscosity (LVT/04/12 RPM@25° C.) of from about 15,000 to 25,000 cps and a weight per gallon of about 7.4 lbs. It can also be diluted with hexane or toluene to a desired solids and/or viscosity range, particularly for use in conventional coating equipment. Other such adhesives which can also be used for these purposes include an acrylic pressure-sensitive adhesive sold by National Adhesives under the designation DUROTAK 80-1054. This adhesive has a solids content of 47.5%, a viscosity of 3,000 cps, and a plasticity (Williams) of 2.9 mm. It is generally used with a solvent system including ethyl acetate, heptane, isopropyl alcohol and toluene. Another such adhesive is sold by Monsanto under the designation GELVA Multipolymer Emulsion 2484, and comprises a stable aqueous acrylic emulsion pressure-sensitive adhesive having a solids content of 59%, and a 40.

Returning to the structure of the active agent carriers shown in the embodiment of FIGS. 4-6, these active agent carriers 112a and 112b again include the active agent contained in a reservoirs 134a and 134b created by backing members 138a and 138b and membranes 132a and 132b, which are again sealed to each other about the perimeter thereof. Active agent permeable adhesive layers 130a and 130b are also employed. Furthermore, the film layers 110a and 110b with layers of active agent impermeable adhesive 136a and 136b thereon are employed. In this manner, the active agent impermeable adhesive layer surrounds at least the periphery of the active agent permeable adhesive layer.

As mentioned above, a primary purpose of the active agent impermeable adhesive layer, such as adhesive layers 9a and 9b, or 136a and 136b, is to provide adhesion to the skin or mucosa, to prevent seepage of the active agent from the device during storage and use, and to maintain the overall film layers against the skin or mucosa surrounding the active agent carriers. Thus, any adhesive which performs these functions will be suitable for use in the present invention. The degree of impermeability of the active agent impermeable adhesive layer to the active agent will vary depending upon the active agent, carrier, transportation agent, etc. Preferably, the active agent impermeable adhesive layer is a pressure sensitive adhesive suitable for contact with the skin or mucosa, e.g., dermatologically acceptable. Examples of suitable pressure sensitive adhesive for use in the present invention as the active agent impermeable adhesive layer include natural rubber adhesive such as R-1072 from B. F. Goodrich Co., No. 735 from C. L. Hathaway, and No. 5702 from Evans St. Clair; acrylic adhesives such as PS-41 from C. L. Hathaway, Vr-0833 from H. B. Fuller, Adcote 73A207A from Morton Chemical, Nos. 80-2404, 80-1054, 72-9056, and 72-9399 from National Starch, Nos. E-2015, E-2067 and E-1960 from Rohm & Haas, M-6112 from Uniroyal, Inc. and Daratak 74 L from W. R. Grace; and synthetic rubber adhesives such as Jowatherm 270-00 and Jowatherm S-3202 from Jowat Corp. and 70-9416 from National Starch.

The width and thickness of the active agent impermeable adhesive layer for contact with the skin or mucosa is that width and thickness which provides at least sufficient impermeability to the active agent (and, if necessary, to the other components of the device with which the impermeable adhesive layer is in contact) so that the active agent does not seep out of the device as explained above. Some suitable widths include 1/16 to 2 inches, and preferably ⅛ to 1 inches. In most instances, the width will be ¼ to ½ inch depending on the specific use. The width and thickness need not be uniform and may vary around the perimeter of the device, e.g., to provide a specific geometric shape or to provide a tab for removal of a protective liner.

The active agent permeable adhesive layers also join the device to the skin or mucosa of the host, but in the case where the active agent carriers are being applied along with the film layers 110a and 110b, as is discussed above, the active agent permeable adhesive layers are used primarily to maintain contact, and thus, it can have less adhesive strength. The adhesive is also preferably dermatologically acceptable. The active agent permeable adhesive layers are also preferably a pressure-sensitive adhesive. Any of the well-known, dermatologically acceptable, pressure-sensitive adhesives which permit drug migration therethrough can be used in the present invention. Some suitable permeable adhesives include acrylic or methacrylic acid (e.g., n-butanol, n-pentanol, isopentanol, 2-methyl butanol, 1-methyl butanol, 1 methyl pentanol, 2-methyl pentanol, 3-methyl pentanol, 2-ethyl butanol, isooctanol, n-decanol, or n-dodecanol esters thereof), alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10 to 24 carbon atoms, glycol diacrylates, or mixture of these monomers; natural or synthetic rubbers such as silicon rubber, styrenebutadiene rubber, butyl-ether rubber, neoprene rubber, nitrile rubber, polyisobutylene, polybutadiene, and polyisoprene; polyurethane elastomers; vinyl polymers, such as polyvinyl alcohol, polyvinyl ethers, polyvinyl pyrrolidone, and polyvinyl acetate; urea formaldehyde resins; phenol formaldehyde resins; resorcinol formaldehyde resins; cellulose derivatives such as ethyl cellulose, methyl cellulose, nitrocellulose, cellulose acetate butyrate and carboxymethyl cellulose; and natural gums such as guar, acacia, pectina, starch, destria, gelatin, casein, etc. The adhesives may also be compounded with tackifers and stabilizers as is well-known in the art.

The active agent permeable adhesive layers preferably contain some of the active agent when the device is placed on the skin. This provides an initial drug presence at the skin or mucosa and eliminates delay in absorption of the active agents or in topical application, if that is desired. Thus, the drugs are immediately available to the host. The initial drug presence may be due to the permeations through the membrane and/or to an amount of the drug mixed in with active agent permeable adhesive layers during manufacture, while on the other hand a surrounding layer of active agent impermeable adhesive serves to limit and clearly define the area of drug administration.

The amount of the active agent present in the permeable adhesive layers depends on the initial drug presence desired, e.g., for a pulse dosage. For example, U.S. Pat. No. 4,031,894 discloses that 10-200 micrograms scopolamine base per $cm^2$ effective surface area is a suitable initial amount of active agent in the permeable adhesive layer.

The width and thickness of the permeable adhesive layer for contact with the skin or mucosa is that width and thickness which provides sufficient permeability to the active agents and a suitable surface area to allow the dosage rates desired to the skin or mucosa. These widths and thicknesses are conventional in the art and therefore need not be discussed in detail here.

Also, the impermeable adhesive layer is in most instances in direct contact and/or adjacent to the permeable adhesive layer. However, this is not necessary and there may be a gap between the permeable adhesive layer and the impermeable adhesive layer if desired.

The thickness and shapes of the permeable and impermeable adhesive layers in the devices of the present invention need not be the same or correspond. This is a particular advantage to the invention in that the device can be made to adhere to specific portions of the skin or mucosa by primary means of the impermeable adhesive layers while not affecting the surface area of the permeable adhesive layer through which the active agent passes (i.e., the shape of the device can be varied without varying the surface area of the membrane and permeable adhesive layer which determines the amount of active agent delivered to the skin or mucosa).

The reservoirs are separated from the permeable adhesive layers by membranes. These membranes may be microporous, in which case the pores become filled with active agents from the reservoirs. The membranes may also function in any other way as long as the active agents permeate through the membranes at a suitable rate. The membranes and the permeable adhesive layers can be monolithic. In this instance, their surfaces are treated to make them adhesive in nature so that they will adhere to the skin or mucosa but still provide membrane permeability characteristics.

The suitability of the rate or permeation of the active agents through the membranes depends on the desired dosage rates and the permeabilities of the active agents through the skin or mucosa. Effective amounts of the active agents are contained in the reservoirs to provide the desired dosages. Sometimes, the skin or mucosa itself determines the rates at which the active agents will be administered therethrough. In these latter instances, if the dosage rates through the skin or mucosa are the dosage rates desired, the membranes need not provide any limiting rates of permeation function but need only supply sufficient active agents to the skin or mucosa to allow the desired permeation through the skin or mucosa which itself determines the dosage rates at which the active agents will be absorbed by the host.

The materials suitable for use as the membrane are conventional in the art and need not be discussed in detail here. Some preferred materials for a separate membrane layers may be, for example, polypropylene, polycarbonates, polyvinyl chloride, cellulose acetate, cellulose nitrate, and polyacrylonitrile. Some suitable encapsulating membrane materials include, for example, hydrophobic polymers such as polyvinyl chloride either unplasticized or plasticized with long-chain fatty amides or other plasticizers, plasticized nylon, unplasticized soft nylon, silicone rubber, polyethylene, and polyethylene terephthalate. Hydrophilic polymers can also be employed such as esters of acrylic and methacrylic acid (e.g., as described in U.S. Pat. Nos. 2,976,576 and 3,220,960 and Belgium pat. No. 701,813); modified collagen; cross-linked hydrophilic polyether gels (e.g., as described in U.S. Pat. No. 3,419,006); cross-linked polyvinyl alcohol; cross-linked partially hydrolyzed polyvinyl acetate; cellulosics such as methyl cellulose, ethyl cellulose, and hydroxyethyl cellulose; and gums such as acacia; carboxymethylcellulose, and carrageenan alone or combined with gelatin.

The active agents suitable for use in the present invention may be, for example, systemic or topical drugs. Individual active agents or mixtures thereof, if desired, can be employed. Any drug which passes through the skin or mucosa can be employed for internal administration in the device of the invention, so long as the drug will pass through the permeable adhesive layers and the material forming the membranes or microcapsules.

Suitable systemic drugs for administration by the claimed device include those useful in treating emesis and nausea as is described in U.S. Pat. No. 4,031,894, e.g., preferably, scopolamine.

Other suitable drugs include the coronary vasodilators describe in U.S. Pat. No. 3,742,951 such as compounds having nitrate moiety. Some suitable coronary vasodilators as well as other suitable systemic drugs are disclosed in U.S. Pat. Nos. 3,996,934 and 4,573,996, and the portions of both of these describing same are incorporated herein by reference thereto.

In the embodiments shown in addition to the active agent carriers, pairs of film layers 10a and 10b, and 110a and 110b, are also utilized. In particular, these film layers are materials which are extremely difficult to handle by themselves and which are intended to act as wound dressings when applied to the skin. Film layers 10a and 10b, or 110a and 110b, or "skin" are thus extremely flimsy materials which preferably allow air and moisture vapor to pass therethrough, but will not permit the passage of bacteria or undesired elements or materials.

It is thus preferred that these film layers thus be composed of various thin, plastic materials, or they can comprise extremely thin foil layers, or layers of other non-woven materials; most particularly they will comprise materials which are sufficiently thin and flexible to be conformable to the skin, and will thus preferably be thinner than about 2 mils, preferably less than about 1.5 mils, and most preferably 1 mil or less.

These film layers are preferably thermoplastic materials which are at least partially elastomeric in nature. They will therefore exhibit a high degree of elongation (preferably greater than about 130% elongation), and will thus exhibit excellent conformability characteristics without having the tendency to exhibit significant memory characteristics, although they will have some degree of recovery when stretched, for example. In terms of being breathable films it is preferred that these materials, in addition to permitting air to pass therethrough, will also permit moisture vapor to pass through them, at least more readily than is the case with materials such as polyethylene, for example. All of these film layers must be occlusive, at least with respect to particulates, in order to protect the wound, etc. However, their overall occlusive characteristics can then vary, depending upon the ultimate use intended for them in each particular case. In general, however, it is preferred that films be employed which are permeable to various glycols, such as polyethylene glycols, but rather occlusive films can also be employed in selected circumstances, including, for example, 1 and 2 mil layers of ethylene-vinyl acetate copolymers, or various nylon or polyester films. In addition, laminated or coated films could also be utilized, such as by employing a non-occlusive film such as those discussed above which is fully or partially selectively coated with an occlusive film.

The various thermoplastic films themselves can generally be produced with either a matte, glossy, or a clear surface, which is obtained by selection or modification of the surface of the chilling roller generally used downstream of the film extruder from which the film is extruded, and they can include various colors, such as skin color, as well as fillers, such as $TiO_2$, clay or other such materials for the purpose of rendering film opaque, and various organic additives, odor inhibitors, and/or various medications, etc. directly on the surface thereof.

From the commercial viewpoint, one of the most successful high moisture vapor permeable medical grade elastomeric films has been one of a series of products marketed by Bertek under the designation "Medifilm 800." These films are extruded from a class of elastomeric resins which are polyether block amides, commercially designated by the trademark PEBAX. The structure of these polymers can be generally represented by the

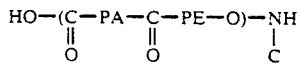

in which PA represents a relatively rigid polyamide segment and PE represents a relatively soft polyether segment. In this manner the extruded film products have high strengths in terms of high tear and abrasion resistance and at the same time provide a high degree of comfort or conformability, as well as moisture vapor permeability. The physical properties of two typical medical grade PEBAX films having a thickness of 1 mil are set forth in TABLE 1 herein.

TABLE I

| PROPERTIES | FILMS | |
|---|---|---|
|  | MEDIFILM 810 | MEDIFILM 827 |
| Tensile strength psi (ASTM D882) | 3120 | 2220 |
| % Elongation | 430 | 800 |
| Modulus @ 50% Elongation | 1600 | 900 |
| Initial tear resistance lbs. (ASTM D-1004) | 0.65 | 0.6 |
| MVTR - g/m2/24 hrs. (ASTM E-96) 37.8 C/90% R.H. | 1675 | 2220 |

In addition, other such film layers can comprise thermoplastic polyurethanes which also meet the above requirements. These include such commercial polyurethane compositions as Dow Chemical Company's PELLETHANE, including its 2363-80AE grade thereof; K. J. Quinn's Q-THANE; B. F. Goodrich's ESTANE; Mobay Chemical Company's TXIN; and others. Furthermore, these film layers 2 can also comprise various polyesters, such as the copolymers of various cyclic polyesters including DuPont's HYTREL, including its 4056 grade thereof, and General Electric's LOMOD, both of which are copolymers of polyether prepolymers and polybutylene terephthalate and polyisobutyl terephthalate, respectively, as well as Eastman Chemical's PCCE.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A device for applying a plurality of active agents to a patient comprising a removable liner layer including a first surface and a second surface, said first surface of said liner layer comprising a releasable surface, a carrier layer including a first surface and a second surface, and a plurality of active agent carrying members disposed on said first surface of said carrier layer, said first surface of said liner layer being releasably heat sealed to said first surface of said carrier layer at least at a location between said plurality of active agent carrying membes so as to physically separate said plurality of active agents prior to removal of said removable liner layer from said carrier layer, whereby removal of said removable liner layer eliminates said heat seal.

2. The device of claim 1 including a plurality of film layers disposed separately on said first surface of said carrier layer between said carrier layer and said plurality of active agent carrying members, each of said plurality of separately disposed film layers being associated with one of said plurality of active agent carrying members, whereby said active agent carrying members are applied to said patient along with said film layers.

3. The device of claim 2 wherein said active agent carrying members comprise adhesive layers admixed with said active agents.

4. The device of claim 2 wherein said adhesive layers carrying said active agents have a thickness of between about 0.5 and 5 mils.

5. The device of claim 1 wherein said first surface of said liner layer is releasably heat sealed to said first surface of said carrier layer at least around the entire periphery of each of said plurality of active agent carrier members.

6. The device of claim 2 wherein said plurality of active agent carrying members comprise a plurality of reservoirs containing said active agent, release means for the controlled release of said active agent from said plurality of reservoirs, and a plurality of active agent impermeable barrier layers between said reservoirs and said carrier layer, whereby said plurality of active agents may only be released from the inner surface of said plurality of reservoirs towards said patient upon application of said plurality of active agent carriers to said patient 7. The device of claim 1 wherein said releasable surface of said liner layer comprises an embossed surface.

8. The device of claim 2 including a first adhesive layer interposed between said first surface of said carrier layer and said plurality of film layers for maintaining said plurality of film layers in contact with said carrier layer when said liner layer is separated from said carrier layer, and a second adhesive layer interposed between said plurality of film layers and said first surface of said liner layer, said first adhesive layer having a first coefficient of adhesion and said second adhesive layer having a second coefficient of adhesion, said first coefficient of adhesion of said carrier layer to said plurality of film layers being less than said second coefficient adhesion of said plurality of film layers to said patient, whereby upon application of said plurality of film layers to said patient with said second adhesive layer therebetween, said plurality of film layers adhere to said patient and said plurality of film layers can be simultaneously removed from said carrier layer 9. The device of claim 8 wherein said second adhesive layer comprises an adhesive layer covering at least the entire surface of said plurality of film layers.

10. The device of claim 1 wherein said releasable surface comprises a siliconized coating 11. The device of claim 1 wherein said liner layer is selected from the group consisting of paper, thermoplastic polymer, foil, and mixtures thereof 12. The device of claim 1 wherein said carrier layer is selected from the group consisting of polyethylene, polypropylene, polyvinylidene chloride, polyethylene terephthalate, polyesters, polyamides, and mixtures thereof.

13. The device of claim 12 wherein said carrier layer comprises polyethylene

14. The device of claim 6 wherein said release means comprises a plurality of active agent permeable membrane layers formed on said inner surface of said plurality of reservoirs whereby said plurality of reservoirs are completely enclosed between said plurality of active agent permeable membrane layers and said plurality of active agent impermeable barrier layers.

15. The device of claim 14, wherein said plurality of active agent impermeable barrier layers extend peripherally beyond said plurality of reservoirs about the entire periphery thereof so as to create extended peripheral areas of said plurality of active agent impermeable barrier layers 16. The device of claim 15 wherein said second adhesive layer includes an active agent permeable adhesive portion and an active agent impermeable adhesive portion, said active agent permeable adhesive portion corresponding to said plurality of active agent permeable membrane layers and said active agent impermeable adhesive portion corresponding to at least said extended peripheral areas of said plurality of active agent impermeable barrier layers 17. The device of claim 6 wherein said release means comprises a plurality of micro-capsules containing said active agent encapsulated by an active agent permeable membrane 18. The device of claim 17 wherein said second adhesive layer includes an active agent permeable adhesive portion corresponding to said inner surface of said plurality of reservoirs.

* * * * *

UNITED STATES PATENT AND TRADEMARK OFFICE
CERTIFICATE OF CORRECTION

PATENT NO. : 5,064,422

DATED : November 12, 1991

INVENTOR(S) : John J. Wick

It is certified that error appears in the above-identified patent and that said Letters Patent is hereby corrected as shown below:

```
Column 1,    line 38, delete "TRANSDER®-NITRO" and insert
             therefor --TRANSDERM®-NITRO--.
             line 56, "disClosed" should read --disclosed--.
Column 3,    line 16, before "simultaneously" insert --the
             patient and the plurality of film layers can--.
Column 5,    line 58, after "the" insert --same--;
             line 58, after "as" insert --are discussed above in
             connection with the film layer 2 and the carrier
             layer 6, preferably comprising extruded
             polyethylene terephthalate, various polyamides, or
             polyvinylidene chloride or SARAN material--.
Column 6,    line 27, "arabinoglactin" should read
             --arabinoglactan--.
Column 7,    line 13, after "been" insert --applied--.
             line 34, delete "player" and insert therefor
             --layer--.
             line 52, delete "38".
Column 9,    line 19, "aqent" should read --agent--.
Column 11,   line 41, before "Returning" insert --viscosity of
             1,500-Z, 300 cps.--.
Column 15,   line 38, after "the" insert --formula:--.
Column 16,   line 33, "membes" should read --members--.
             line 66, after "patient" insert --.--.
Column 17,   line 19, after "layer" insert --.--.
             line 25, after "coating" insert --.--.
             line 28, after "thereof" insert --.--.
```

UNITED STATES PATENT AND TRADEMARK OFFICE
CERTIFICATE OF CORRECTION

PATENT NO. : 5,064,422

DATED : November 12, 1991

INVENTOR(S) : John J. Wick

It is certified that error appears in the above-identified patent and that said Letters Patent is hereby corrected as shown below:

Column 18, line 2, after "polyethylene" insert --.--.
          line 15, after "layers" insert --.--.
          line 24, after "layers" insert --.--.
          line 28, after "membrane" insert --.--.

Signed and Sealed this

Sixth Day of April, 1993

Attest:

STEPHEN G. KUNIN

*Attesting Officer*     *Acting Commissioner of Patents and Trademarks*